(12) United States Patent
Huang et al.

(10) Patent No.: US 11,583,226 B2
(45) Date of Patent: Feb. 21, 2023

(54) METHOD AND SYSTEM OF MONITORING AND ALERTING PATIENT WITH SLEEP DISORDER

(71) Applicants: Kelly Huang, San Dimas, CA (US); Lina Huang, San Dimas, CA (US)

(72) Inventors: Kelly Huang, San Dimas, CA (US); Lina Huang, San Dimas, CA (US)

(*) Notice: Subject to any disclaimer, the term of this patent is extended or adjusted under 35 U.S.C. 154(b) by 31 days.

(21) Appl. No.: 17/216,630

(22) Filed: Mar. 29, 2021

(65) Prior Publication Data

US 2021/0275087 A1    Sep. 9, 2021

Related U.S. Application Data

(63) Continuation-in-part of application No. 16/734,355, filed on Jan. 5, 2020, now Pat. No. 10,964,195.

(51) Int. Cl.
*A61B 5/00* (2006.01)
*A61B 5/0205* (2006.01)

(52) U.S. Cl.
CPC .......... *A61B 5/4806* (2013.01); *A61B 5/0205* (2013.01); *A61B 5/4839* (2013.01); *A61B 5/7264* (2013.01); *A61B 5/746* (2013.01); *A61B 5/747* (2013.01)

(58) Field of Classification Search
CPC ... A61B 5/4806; A61B 5/0205; A61B 5/4839; A61B 5/7264; A61B 5/746; A61B 5/747
USPC ....................................................... 340/575
See application file for complete search history.

(56) References Cited

U.S. PATENT DOCUMENTS

| | | | | |
|---|---|---|---|---|
| 5,117,096 A | * | 5/1992 | Bauer | G05B 19/4183 705/28 |
| 5,278,190 A | * | 1/1994 | Askanazi | A61K 31/195 514/561 |
| 2005/0037449 A1 | * | 2/2005 | Doi | A61P 15/00 514/17.7 |
| 2008/0081961 A1 | * | 4/2008 | Westbrook | A61B 5/14551 600/301 |
| 2008/0269629 A1 | * | 10/2008 | Reiner | A61B 5/6831 600/544 |
| 2008/0275349 A1 | * | 11/2008 | Halperin | A61B 5/447 600/364 |
| 2010/0007219 A1 | * | 1/2010 | de Buda | H04B 3/546 307/149 |
| 2011/0132378 A1 | * | 6/2011 | Levendowski | A61B 5/1116 128/848 |
| 2011/0253884 A1 | * | 10/2011 | Ottleben | G01V 8/20 250/221 |

(Continued)

*Primary Examiner* — Kerri L McNally
*Assistant Examiner* — Thang D Tran (57) ABSTRACT

A method and a system of alerting and/or monitoring patient with sleep disorder includes: a detector for detecting a change in a first parameter, a storage device, a control unit for deciding if the change meets a set criteria, and if the change meets the set criteria, saving the first parameter and/or time in the storage device, a feedback unit for adjusting the set criteria according to sleep behavior of the patient, and an alarm device for sending an alarm, wherein the first parameter includes sound, motion, heart rate, blood pressure, breathing frequency, magnitude and/or frequency of movement, muscle activity, brain activity, eye movements, heart rhythm, heart rate variability, blood oxygen levels, breathing pattern, and/or body position.

18 Claims, 5 Drawing Sheets

Detecting a change in a parameter

Sounding an alarm (56) References Cited

U.S. PATENT DOCUMENTS

| | | | |
|---|---|---|---|
| 2014/0278139 A1* | 9/2014 | Hong | G01C 22/006 |
| | | | 702/19 |
| 2015/0031964 A1* | 1/2015 | Bly | A61B 5/681 |
| | | | 600/300 |
| 2015/0164721 A1* | 6/2015 | Miyashita | G06V 40/161 |
| | | | 5/617 |
| 2016/0007916 A1* | 1/2016 | Iwawaki | A61B 5/7214 |
| | | | 600/479 |
| 2016/0022193 A1* | 1/2016 | Rau | A61B 5/165 |
| | | | 600/595 |
| 2016/0198129 A1* | 7/2016 | Proud | A61B 5/1118 |
| | | | 348/143 |
| 2016/0367184 A1* | 12/2016 | Lim | G16H 50/30 |
| 2016/0367188 A1* | 12/2016 | Malik | G16H 40/67 |
| 2017/0135632 A1* | 5/2017 | Franceschetti | A61B 5/725 |
| 2017/0347950 A1* | 12/2017 | Jones | A47C 27/064 |
| 2018/0125256 A1* | 5/2018 | Tsern | A47C 27/082 |
| 2018/0132789 A1* | 5/2018 | Chen | A61B 5/02438 |
| 2018/0133480 A1* | 5/2018 | Annoni | A61N 1/0551 |
| 2019/0000350 A1* | 1/2019 | Narayan | A61B 5/08 |
| 2019/0001117 A1* | 1/2019 | Ben-David | A61B 5/4812 |
| 2019/0008450 A1* | 1/2019 | Gurievsky | A61B 5/4812 |
| 2019/0008577 A1* | 1/2019 | Lazarus | A61B 18/02 |
| 2019/0132948 A1* | 5/2019 | Longinotti-Buitoni | |
| | | | A61B 5/743 |
| 2019/0223781 A1* | 7/2019 | Arrington | A61B 5/7455 |
| 2020/0188671 A1* | 6/2020 | Lovett | A61B 5/686 |
| 2020/0335211 A1* | 10/2020 | Gopalakrishnan | G16H 40/20 |
| 2021/0267523 A1* | 9/2021 | Donoghue | A61N 1/0504 |
| 2022/0007965 A1* | 1/2022 | Tiron | A61B 5/6898 |

* cited by examiner

METHOD AND SYSTEM OF MONITORING AND ALERTING PATIENT WITH SLEEP DISORDER

CROSS-REFERENCE TO RELATED APPLICATION

This application is a continuation-in-part of U.S. application Ser. No. 16/734,355, filed on Jan. 5, 2020, the entire content of which is incorporated herein by reference.

FIELD

The present disclosure is related to a method and a system of monitoring and/or alerting patient(s) with sleep disorder.

BACKGROUND

Patients with sleep disorder, such as rapid eye movement sleep behavior disorder (RBD) or sleep terror, have the potential to be injured or have disrupted sleep behavior, indicated by talking, laughing, shouting, gesturing, grabbing, flailing, punching, kicking, sitting up, and/or leaping from bed. Sometimes vigorous, violent episodes may occur.

For example, RBD is typically characterized by abnormal or disruptive behaviors emerging during the rapid eye movement (REM) sleep stage. Most people are paralyzed during this sleep period; however, RBD patients are not and therefore can act out their dreams. These actions can include shouting, kicking, running, etc., which may cause serious injury and/or harm to themselves, and/or disruptions to others nearby (e.g., sleep partners).

In contrast to sleep walking, patients with RBD can be easily woken up with even small noises. However, many RBD patients live alone, and may not be able to be alerted until injured by their movements.

The medical treatments for RBD (e.g., medications) are not always effective, and may also have undesirable side effects.

Also, for example, in patients with obstructive sleep apnea (OSA), the soft tissue in the back of the throat collapses and blocks the airway, which leads to partial reductions in breathing, commonly referred to as "hypopneas". This can lead to complete pauses in breathing, which are often referred to as "apneas." In children, these obstructions tend to occur during the rapid eye movement (REM) sleep stage. OSA may cause the patient to have low levels of oxygen in the blood. While adults with OSA may wake up easily after their breathing stops, children with OSA often do not wake up in response to pauses in breathing. OSA may lead to deformation of the chest, such as depression in the chest wall, abnormal sleep positions, and other health issues and/or behavior issues. For example, patients with OSA may suffer from high blood pressure, heart disease, stroke, pre-diabetes and diabetes, and depression.

As such, there is a need for helping patients with sleep disorder, such as RBD or OSA, to avoid harm or injury.

SUMMARY

An aspect of the present disclosure is directed toward a method of monitoring and/or alerting a patient with sleep disorder, for example, patient with rapid eye movement (REM) sleep behavior disorder (RBD).

Another aspect of the present disclosure is directed toward a system for monitoring and/or alerting a patient with sleep disorder, e.g., an RBD patient.

Other aspects will be set forth in the descriptions below, and will be clear from the description, or may be learned by practice of the presented embodiments.

According to an embodiment, a method of alerting, preventing injury, and/or monitoring of patient(s) with sleep disorder includes: detecting a change in a parameter(s), and if the change is detected, sounding an alarm, wherein the parameter(s) includes sound, motion, heart rate, blood pressure, breathing frequency, magnitude and/or frequency of movement, muscle activity, brain activity, eye movements, heart rhythm, heart rate variability, blood oxygen levels, breathing pattern, and/or body position.

This method aids in preventing the patient from injury and/or harm in that it senses parameters indicative of injury-causing actions and alerts the patient before those actions occur (e.g., before the patient leaves the bed).

The method may further include deciding if the change meets a set criteria, and if the change meets the set criteria, sounding the alarm.

The set criteria may be adaptable to sleep behavior of the patient.

The parameter may be sound, and the set criteria may include a pitch and/or volume of the sound.

The parameter may be motion, and the set criteria may include a range, speed, and/or a frequency of the motion.

The parameter may be heart rate, and the set criteria may include a threshold value of the heart rate.

The parameter may be blood pressure, and the set criteria may include a threshold value of the blood pressure.

The parameter may be magnitude and/or frequency of movement, and the set criteria may include a threshold value of the magnitude and/or frequency of movement.

The parameter may be breathing frequency, and the set criterial may include an interval between adjacent breathes.

The method may further include detecting a time duration of the change in the parameter, and the set criteria may include a threshold value of the time duration.

The alarm may include a customizable message.

The method may further include establishing a customized reference value for the parameter for an individual (e.g., a specific) patient.

The method may further include attaching a device to the patient, wherein the device is to detect the parameter and/or sound the alarm.

According to an embodiment, a system of alerting/preventing injury and/or monitoring of patient with sleep disorder, such as RBD, includes a detector for detecting a change in a parameter(s) and an output device for sounding an alarm, wherein the parameter(s) comprise(s) sound, motion, heart rate, blood pressure, breathing frequency, magnitude and/or frequency of movement, muscle activity, brain activity, eye movements, heart rhythm, heart rate variability, blood oxygen levels, breathing pattern, and/or body position.

The system may further include a control unit for deciding if the change meets a set criteria, and if the change meets the set criteria, sounding the alarm.

The detector may be a heart rate monitor, a motion sensor, an audio sensor/detector, a blood pressure sensor, an electromyogram (EMG), an electroencephalogram (EEG) machine, an electrooculogram (EOG), an electrocardiogram (ECG or EKG), and/or a pulse oximeter.

The control unit may adapt the set criteria according to sleep behavior of the patient and/or user feedback.

The control unit may include a codable device.

The control unit may communicate with a remote device (e.g., a smartphone, a smartwatch, a laptop).

The remote device may have a customizable program to display data, set values, track history, obtain user feedback, and/or communicate with other devices.

The output device may be a speaker and/or vibrating device. The output device may be customizable (e.g., message, volume, duration, tone).

According to embodiments of the present disclosure, a system of alerting and/or monitoring patient with sleep disorder includes: a detector for detecting a change in a first parameter, a storage device, a control unit for deciding if the change meets a set criteria, and if the change meets the set criteria, saving the first parameter and/or time in the storage device, a feedback unit for adjusting the set criteria according to sleep behavior of the patient, and an alarm device for sending an alarm, wherein the first parameter includes sound, motion, heart rate, blood pressure, breathing frequency, magnitude and/or frequency of movement, muscle activity, brain activity, eye movements, heart rhythm, heart rate variability, blood oxygen levels, breathing pattern, and/or body position.

According to embodiments of the present disclosure, a method of monitoring patient condition with sleep disorder includes detecting the change in the first parameter utilizing the system according to embodiments of the present disclosure, deciding if the change meets the set criteria, and storing the first parameter and/or time in the storage device if the change meets the set criteria.

A method of monitoring treatment effect for patient with sleep disorder includes detecting the change in the first parameter utilizing the system according to embodiments of the present disclosure, deciding if the change meets the set criteria, and storing the first parameter and/or time in the storage device if the change meets the set criteria.

The method may further include collecting a first dataset comprising a plurality of parameters, conducting a learning process in machine learning to select one or more parameters to constitute the first parameter and a set criteria for each of the one or more parameters, and monitoring the patient utilizing only the first parameter and the set criteria in the detecting of the change in the first parameter utilizing the system according to embodiment of the present disclosure, wherein the plurality of parameters includes 3 or more selected from sound, motion, heart rate, blood pressure, breathing frequency, magnitude and/or frequency of movement, muscle activity, brain activity, eye movements, heart rhythm, heart rate variability, blood oxygen levels, breathing pattern, and body position.

DETAILED DESCRIPTION

According to embodiments of the present disclosure, a method and a system of alerting patient with sleep disorder are provided.

Figure 1:
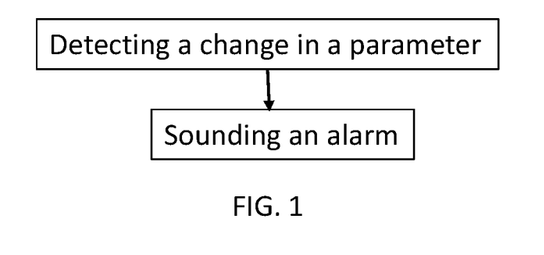
FIG. 1 is a flow chart illustrating a method of alerting a patient with sleep disorder according to an embodiment of the present disclosure.
Figure 2:
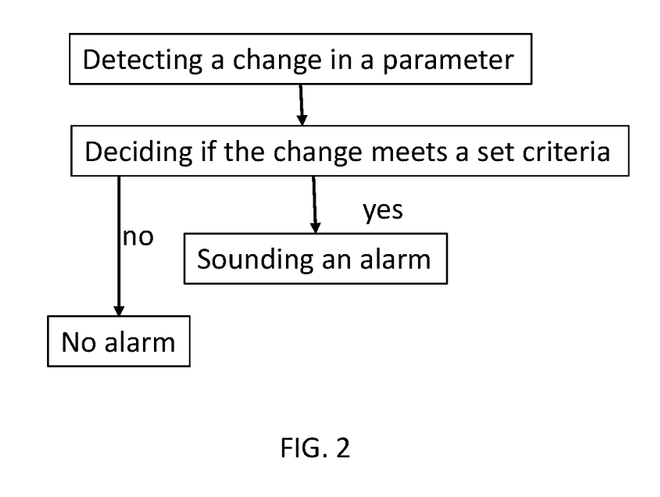
FIG. 2 is a flow chart illustrating a method of alerting a patient with sleep disorder according to an embodiment of the present disclosure.

FIGS. 1 and 2 are each a flow chart illustrating a method of alerting a patient with sleep disorder. Referring to FIG. 1, according to an embodiment, a method of alerting, preventing injury and/or monitoring a patient with sleep disorder, such as RBD, includes: detecting a change in a parameter(s) and sounding an alarm, wherein the parameter(s) includes sound, motion, heart rate, blood pressure, breathing frequency, magnitude and/or frequency of movement, muscle activity, brain activity, eye movements, heart rhythm, heart rate variability, blood oxygen levels, breathing pattern, and/or body position.

Referring to FIG. 2, the method may further include deciding if the change meets a set criteria, and if the change meets the set criteria, sounding the alarm.

During sleep, the patient (e.g., an RBD patient) may have a dream (e.g., nightmare) in which the patient may act out the dream, using hands and arms for dramatic motions, speaking in relation to the dream scene, and/or rolling or jumping off the bed. Without being conscious of their surroundings, they may bump into things such as the bed frames, other furniture around them, doors, fall into bath tubs, and/or disrupt others nearby.

To avoid patient injury, a detector (e.g., a sensor, a monitoring device, etc.) may be utilized to detect and/or monitor the parameters that change or manifest during times of abnormal action in sleep, such as sound (e.g., shouting, yelling, crying, etc., of the patient), motion (e.g., waving of the arms, kicking, turning the body, etc.), heart rate, blood pressure, breathing frequency, magnitude and/or frequency of movement (e.g., of arms, legs, head, etc.), muscle activity (or skeletal muscle activation) (e.g., muscle contraction), brain activity (e.g., change in electrical brain activity), eye movements (e.g., frequency and/or magnitude of eye movement), heart rhythm, heart rate variability, blood oxygen levels, breathing pattern, and/or body position.

The detector may be installed at a location near the patient, such as on the wall near the bed, on the bed (e.g., bed frame), coupled to a smartphone, or may be a wearable device worn on the patient (e.g., wrist, arm, ankle, leg, finger, foot, hand, head, ear, etc.), or attached to the patient (e.g., through pajamas, socks, etc.).

The parameter may be sound, and the set criteria may include pitch, frequency, intensity, and/or volume of the sound. For example, when the patient starts screaming or talking excitedly, the detector may detect the pitch, frequency, intensity, and/or volume (e.g., the change in the pitch, frequency, intensity, and/or volume from prior to the screaming or talking). Furthermore, the detected pitch, frequency, intensity, and/or volume of sound may be compared with a set criteria, such as the pitch, frequency, intensity, and/or volume of normal speaking voice of the patient, the background noise of the patient's living conditions, and/or normal snoring sound of the patient. If the detected pitch, frequency, intensity, and/or volume exceeds the set criteria, the patient alert system may sound an alarm to wake the patient. For example, if the patient screams, the system will detect the change in the sound, e.g., increased volume, shifting of sound frequency and/or pitch from the normal speaking voice of the patient, and activate the alarm. In some embodiments, the system will sound the alarm when a change in volume of about 30 dB, 40 dB, or 50 dB or greater is detected. In other embodiments, the system will sound the alarm when a change in frequency of about 100 Hz, 200 Hz, or 250 Hz or greater is detected.

In one embodiment, the patient alert system including the detector may take the normal snoring sound and normal (peaceful) speaking sound of the patient as the baseline sound. The system may be set so that the set criteria is above the baseline sound of the patient with an adaptable tolerance. Accordingly, the system may not sound the alarm when no change that meet the set criteria (e.g., no sound that exceeds the baseline sound) is detected. In this case, the normal sleep talking (e.g., non-violent episodes) or snoring will not trigger the alarm.

In one embodiment, the sensitivity of the detector may be set to be above the baseline sound, such that the alarm will sound only when the sound exceeds the baseline sound in one or more of the pitch, frequency, intensity, volume, etc.

The set criteria may be customized according to the habits and/or normal state of the patient, and may be determined based on the individual symptoms so that the alarm will sound when the patient's dream has progressed to injury-causing scenarios, but it will not sound when the patient is dreaming in a peaceful manner that will not lead to dangerous episodes. For example, the patient alert system may have a number of trigger levels, and the patient and/or caregiver may choose the trigger level through trial and error and/or by measuring/observing the patient's states.

The parameter may be motion, and the set criteria may include a speed, an acceleration, and/or a frequency of the motion. In an embodiment, the movement may include limb movement, head movement, chest movement and/or abdominal movement. For example, when the system detects the patient waving their arms and/or kicking violently (e.g., at a frequency, range, or magnitude above normal sleep activity), it may sound the alarm. However, movements that are not likely to cause harm and/or injury to the patient (e.g., peacefully switching sides, occasional turning) during sleep may not trigger the alarm. In some embodiments, the system will sound the alarm when a motion with a speed of about 3 m/s, 4 m/s or 5 m/s or greater is detected. In other embodiments, the system will sound the alarm when a motion with an acceleration of about 7 m/s$^2$, 8 m/s$^2$, 9 m/s$^2$, or 10 m/s$^2$ or greater is detected. In other embodiments, the system will sound the alarm when a frequency of the movement is 1 Hz, 2 Hz, or 3 Hz or greater is detected (e.g., changed from no movement).

The parameter may be heart rate, and the set criteria may include a threshold value. For example, when the patient moves their arms and/or legs violently or when the patient dreams of a violent scenario, their heart rate may be significantly different, e.g., higher or lower than the normal rate of heart rate during sleep. The heart rate may be monitored through an electrocardiogram on the patient (e.g., on the chest). The set criterial may be a heart rate value that is different (e.g., 10%, 20%, or 30% more or less and/or 10 beats per minute, 20 beats per minute, or 30 beats per minute more or less) from the normal sleep heart rate.

The parameter may be blood pressure, and the set criteria may include a threshold value. The blood pressure may be monitored through a blood pressure gauge, a continuous wave radar, or arterial catheter on the patient (e.g., on the wrist), and the threshold value may be significantly lower or higher than the normal blood pressure of the patient, such as 3%, 5%, 10% or 15% lower or higher. This monitoring device may measure the systolic pressure, diastolic pressure, or both. The alarm may be integrated with the monitoring device (e.g., blood pressure gauge, arterial catheter), or may be separate and/or located at a location different from the monitoring device.

The parameter may be breathing frequency, and the set criteria may include a threshold value. For example, if the patient is breathing below or above the threshold frequency, such as a decreased or increased rate of 10%, 15%, 20%, etc., the change in frequency may trigger the alarm.

The parameter may be magnitude and/or frequency of the movement, and the set criteria may include a threshold value. For example, if the patient waves arms, kicks legs, and/or turns the body 2 times or more in a set time frame, such as 10 seconds, 30 seconds, 1 minute, etc., the increased frequency of movement may trigger the alarm.

The parameter may be the orientation of the patient's body. For example, when the patient changes from one lying position to another position that is 15° or more in angle from the original lying position, or change from a lying position to sitting up or standing position, the sensor may sense the change in the body orientation and trigger the alarm.

The parameter may be the electromyography (EMG) signal on muscle activity, electroencephalography (EEG) and/or functional magnetic resonance imaging (fMRI) signal on brain activity, electrooculography (EOG) signal on eye movements, electrocardiography (ECG or EKG) on heart rhythm or heart rate variability, pulse oximeter data on blood oxygen levels, and/or breathing pattern. For example, if any one of these parameters changes by 5%, 10% or 15% or less or greater in magnitude and/or frequency, the sensor may sense the change and trigger the alarm.

In one embodiment, two or more of the parameters may be utilized together. For example, two or more selected from sound (e.g., shouting, yelling, crying, etc., of the patient), motion (e.g., waving of the arms, punching, kicking, fast turning of the body, standing, etc.), heart rate, blood pressure, breathing frequency, magnitude and frequency of movement (e.g., of arms, legs, head, etc.), muscle activity, brain activity, eye movements, heart rhythm, heart rate variability, blood oxygen levels, breathing patterns, and body position may be utilized together in detecting the state of the patient in sleep and the controller triggers the alarm based on the two or more detected parameters.

The method may further include detecting a time duration of the change in the parameter, and the set criteria may include a threshold value of the time duration. For example, when the patient tosses and turns for a set time duration, the alarm may sound. In one embodiment, even when the movement is in a smaller magnitude, if the movement happens more than a set number during a set period, the alarm may sound. For example, if the motion happens more than three times in 5 seconds, 10 seconds, etc., the alarm will sound.

In one embodiment, for a patient with OSA, the parameter may be breathing frequency and the set criteria may include a reduction in the breathing frequency. If the patient has stopped breathing for a set period of time, such as 5 seconds, 10 seconds, etc., the alarm may sound.

In some embodiments, the alarm may include a customizable sound. The sound may be an alarm tone, such as a ringing sound, etc.

In another embodiment, the alarm may include a customizable message. The customizable message may be a desired message for the patient, such as a close family member's voice saying "wake up," "mom," "dad," etc. The customizable message may also be a phrase chosen by the patient, such as one from a favorite song lyric, a phrase from the Bible, a movie line, a quote, etc.

In another embodiment, the alarm may be physical vibration and/or action (i.e. shaking the bed), or both physical vibration and sound. The alarm may be included in a wearable device such that when triggered, the physical vibration and/or action can provide the stimulation to wake up the patient.

The method may further include establishing a reference (e.g., a baseline) value for the parameter for a specific patient. For example, the patient and/or caregiver may monitor the symptoms of the patient and establish the correlation between the voice, motion, heart rate, blood pressure, magnitude and/or frequency of movement, muscle activity, brain activity, eye movements, heart rhythm, heart rate variability, blood oxygen levels, and/or breathing patterns and the likelihood of the patient engaging in endangering actions, such as jumping off the bed, falling off the bed, hitting the bed frame, etc. This may also include symptoms of the patient that establish the correlation between the voice, motion, heart rate, blood pressure, breathing frequency, magnitude and/or frequency of movement, muscle activity, brain activity, eye movements, heart rhythm, heart rate variability, blood oxygen levels, and/or breathing patterns and the likelihood of the patient engaging in disruptive actions, such as shouting, pounding on the bed, etc. The set criteria can then be established so that it will accurately indicate the endangering actions before the patient actually hurt himself/herself.

The method may further include putting a device on the patient, wherein the device is to detect the parameter(s) and/or sound the alarm. For example, the device may be put on the patient's wrists, ankles, fingers, chest, feet, arms, legs, forehead, etc., through a belt, wrist band, or through attachment to socks, gloves, pajamas, eye mask, hairband, etc.

FIGS. 3A-3D schematically show a method of alerting a patient with sleep disorder according to an embodiment of the present disclosure.

Figure 3A:
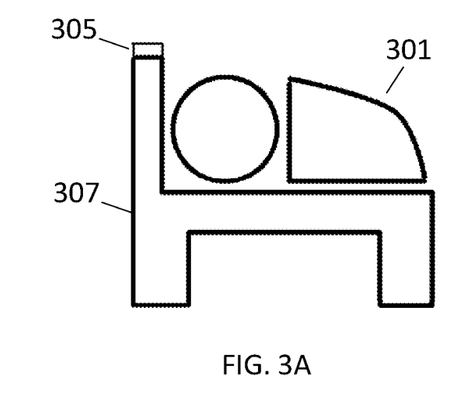
FIGS. 3A-3D schematically show a method of alerting a patient with sleep disorder according to an embodiment of the present disclosure.
Figure 3B:
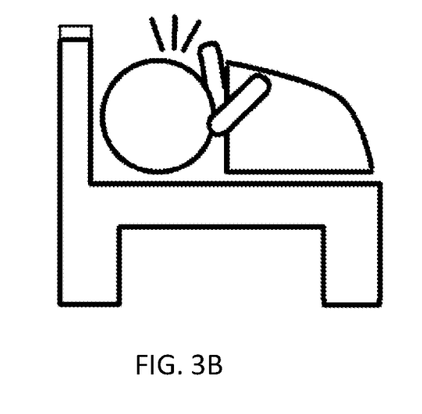
Figure 3C:
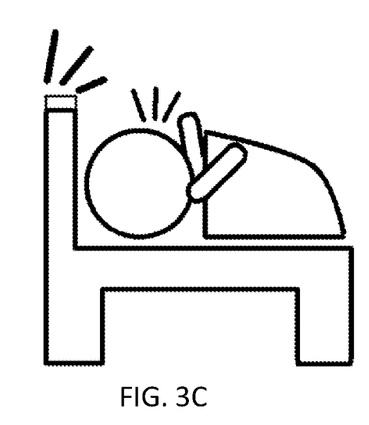
Figure 3D:
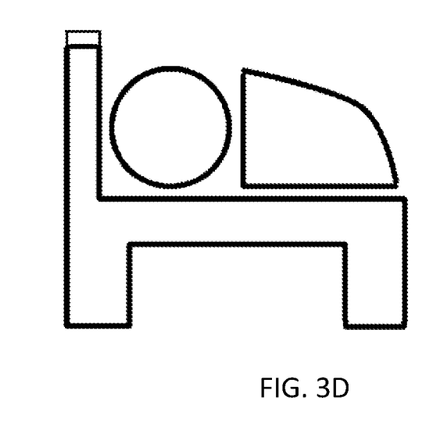

Referring to FIGS. 3A-3D, the patient 301 initially sleeps peacefully in bed 307, and the patient alert system 305 does not sound any alarm (FIG. 3A). The patient 301 then starts making moves (e.g., waving arms) and/or shouting during an abnormal sleep stage (FIG. 3B). The change in the motion and/or sound above the set criteria is detected by the detector of the patient monitoring system 305 near the patient 301, and the patient alert system 305 sounds an alarm (FIG. 3C) to wake the patient 301 from sleep to avoid the patient from hurting himself/herself with more violent moves, jumping off the bed, etc. Once the patient is awake, the patient resets the alarm and falls back to a peaceful sleep (FIG. 3D).

Figure 4:
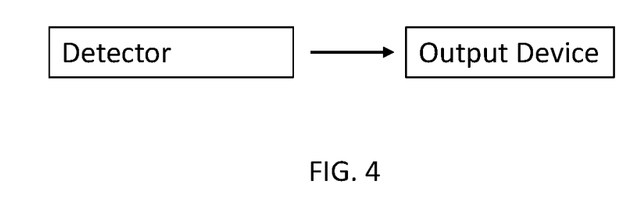
FIG. 4 is a schematic illustration of a system for altering a patient with sleep disorder according to an embodiment of the present disclosure.
Figure 5:
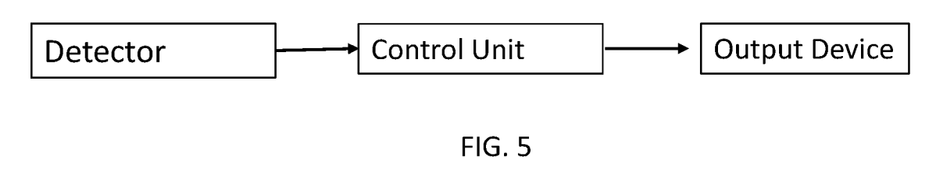
FIG. 5 is a schematic illustration of a system for altering a patient with sleep disorder according to an embodiment of the present disclosure.

FIGS. 4 and 5 are each a schematic illustration of a system for altering a patient with sleep disorder. Referring to FIG. 4, according to an embodiment, a system of alerting, preventing injury and/or monitoring of patient with sleep disorder, such as RBD, includes a detector for detecting a change in a parameter(s) and an output device for making an alarm, wherein the parameter(s) includes sound, motion, heart rate, blood pressure, breathing frequency, magnitude and/or frequency of movement, muscle activity, brain activity, eye movements, heart rhythm, heart rate variability, blood oxygen levels, breathing pattern, and/or body position.

Referring to FIG. 5, the system may further include a control unit for deciding if the change meets a set criteria, and if the change meets the set criteria, triggering the output device to sound the alarm.

The detector may be a heart monitor (a heart rate monitor, an electrocardiogram, etc.), a motion detector (motion sensor, Passive Infrared (PIR) sensor, etc.), a sound detector (an audio sensor, a microphone, etc.), an accelerometer (tilt sensor), a global positioning system (GPS), an optical heart rate monitor, a pulse oximeter, an electromyograph, an electroencephalogram machine, an electrooculogram, a thermometer, a bioimpedance sensor, and/or a blood pressure sensor. However, the present disclosure is not limited thereto, and any suitable sensor for sensing the related parameters may be utilized in the system according to embodiments of the present disclosure.

The control unit may include a central processor unit (CPU), a codable device, etc. For example, the control unit may be an Arduino board, a Raspberry Pi, an integrated circuit board, or any suitable processor where the input is a signal from the detector, and the output is the alarm. The control unit may be programmed utilizing any suitable programming language, such as Python, Java, C, C#, Ruby, Hypertext Preprocessor (PHP), Objective-C, JavaScript, etc. However, the present disclosure is not limited thereto, and any suitable control unit, controller, control board, or processor for receiving the input from the sensor and providing signal to the output device may be utilized in the system according to embodiments of the present disclosure.

The control unit may communicate with a remote device (e.g., a smartphone, a smartwatch, a laptop). The remote device may have a customizable program (e.g., smartphone application) to display data, set values, track history, and/or communicate with other devices.

The output device may be a speaker, a buzzer, or any suitable sound making device, and/or a vibrating device.

The speaker may be customizable (e.g., message, volume, tone, duration of sound). For example, the speaker may provide a customizable message that alerts, wakes, soothes, and/or comforts the patient.

In one embodiment, the detector, the control unit and the output device may all be included in one unit. For example, the detector, the control unit, and the output device may all be included together inside one case (e.g., housing). In another embodiment, the detector, the control unit and the output device may be separated from one another. For example, the detector may be located on and/or near the patient, and the control unit and the output device may be located further away from the patient. In another embodiment, the detector and the control unit are included together inside one case, and the output device may be located in a different place.

According to another embodiment, the system may further include a display showing the parameter detected, a memory device for recording the parameter detected throughout the night, and/or a communication part for sending the recorded information to another device, such as a computer, a smartphone, a tablet, etc. For example, the patient and/or caregiver may review the information recorded during the sleep period, and track the severity of sleep disorder, the development of the sleep disorder, and link it to the behavior of the patient during the sleep period. The patient and/or caregiver may set the criteria for sounding the alarm according to the analysis of the recorded information.

According to one embodiment, the detector may include a unit to send the detected parameter to another device, such as a smartphone, through wireless communication. The control unit and the alarm may be implemented using the smart phone system through an application (e.g., an app). In an embodiment, the detected parameter may be sent to a smartphone via Bluetooth Low Energy (BLE). The smartphone may store the information in a custom-made smartphone app. In one embodiment, the detector may be coupled to more than one device; for example, the detector may be coupled to both the patient's smartphone and a caregiver's smartphone such that both the patient and the caregiver can receive the information about the patient's sleep status.

The system may further include a suitable power source, such as a battery pack or a battery. For example, the system may be powered by a coin cell battery, an AA battery, a AAA battery, or multiple batteries, or powered through plug into a power outlet or through a solar energy system.

The system may further include an attachment part, such as a magnet, Velcro, belt, etc., for attaching to a fixture and/or the patient.

The system according to embodiments of the present disclosure may alert a patient with sleep disorder before the patient leaves the bed. By identifying and detecting the parameters that are indicative of an injury-causing scenario in the patient's sleep, the system wakes the patient before the patient causes harm to himself/herself. For example, the system detects the screaming, shouting, and/or forceful movement of the patient, and wakes the patient while he/she is still in bed. Furthermore, the system may be customized to suit the behavior pattern of each patient to reduce or minimize false alarms.

According to embodiments of the present disclosure, a system and a method for monitoring abnormal sleep behavior for providing reliable and accurate information to aid physicians in diagnosis, research and treatment of sleep disorder conditions are provided. The system identifies and detects the parameters that are indicative of an abnormal sleep behavior (e.g., an injury-causing scenario in the patient's sleep), magnitude of activity, length of activity, and/or the time (e.g., time of the day and the date), and the number of occurrences of the abnormal sleep behavior are stored in a device, such as a smartphone, a computer, a tablet, etc., through wired, wireless, or USB communication. The system may be substantially the same as the system described above. In an embodiment, each time the detected parameter is over a set criteria (e.g., the change in the parameter meets the set criteria), the system stores information such as the detected parameter, and/or the time of the day and the date in the storage device as one occurrence of the sleep disorder event. In an embodiment, each time the system detects an occurrence of the sleep disorder event, the system may send a notification to another device, such as a smartphone, to inform family members, physicians, etc., of the patient's frequency of having sleep disorder event. Throughout the present disclosure, the sleep disorder event includes one that if uninterrupted, will lead to undesirable results, such as injuries to patient or bed partner, long-term health effects, etc. Throughout the present specification, the terms "set criteria" and "threshold value" are used interchangeably.

In an embodiment, the system may track and store total hours of sleep (e.g., total hours the detector is on), number of episodes of sleep disorder (e.g., total number of times the set criteria is reached), length of episode of sleep disorder (e.g., duration of time when set criteria is reached), magnitude and type of activity during episodes per night, week, month, year, etc. The recorded information may be displayed and/or analyzed.

In some embodiments, the system for tracking abnormal sleep behavior may include a detector for detecting a change in a parameter, a control unit for deciding if the change meets a set criteria, and a storage and display device for storing the abnormal sleep behavior activity and time, wherein the parameter may include sound, motion, heart rate, blood pressure, breathing frequency, magnitude and/or frequency of movement, muscle activity, brain activity, eye movements, heart rhythm, heart rate variability, blood oxygen levels, breathing pattern, and/or body position as disclosed above. In an embodiment, the storage device and display device may be separate devices. In an embodiment, the system may not include a device for sounding the alarm. In another embodiment, the device for sounding the alarm may be disabled during the patient monitoring period, and may be turned on during the patient alerting period.

In related art, the diagnosis of abnormal sleep behavior relies on monitoring the patient in the hospital at night, which may lead to change in patient's sleep behavior due to the changed environment. In other occasions, the diagnosis and monitoring relies on recount from patients themselves or their bed partners, caregivers, or family. However, due to the fact that these events happen during sleep, there may be inaccuracy in the patient's and/or caregiver's statement. Also in the case of RBD, a significant percentage of patients eventually develop Parkinson's disease, which makes the recounting of abnormal sleep behavior even more challenging, particularly those sleeping alone. With the system and method described herein, the abnormal sleep behavior can be accurately tracked and monitored in a home environment, and the information provided to the physicians can aid in accurate diagnosis of sleep disorder conditions. The physician may also determine if intervention is needed more urgently or not depending on the record provided by the system.

In some embodiments, the method includes detecting the number of occurrences of abnormal sleep behavior utilizing the system, storing the information and utilizing the stored information in diagnosis. In some embodiments, the date and time of the occurrence and/or abnormal sleep behavior activity may be displayed as a list, a table, a graph, a bar chart, or similar formats. Utilizing the current patient monitoring system, physicians do not need to watch video recordings and other parameters collected over the entire night or multiple nights to identify whether an abnormal sleep behavior has happened, the severity of it, or to characterize abnormal sleep behavior. The display would enable patients and physicians to easily view a summary of abnormal sleep behavior activity (e.g., type of activity, parameter value, magnitude of activity, time of activity, frequency, length of activity) over a period of time (e.g., weeks, months, years, etc.).

In some embodiments, a video recording system is utilized concurrently with the patient monitoring system. The physician, caregiver or party of interest may identify the portion of video to watch based on the information on the patient monitoring system to save time and to not miss any occurrence of the sleep disorder events.

According to embodiments of the present disclosure, a system and a method for monitoring effects of medical treatment on abnormal sleep behavior that provide reliable and accurate information to aid physicians in creating and changing treatment plans are provided. The system is substantially the same as the system described above, where the system identifies and detects the parameters that are indicative of an abnormal sleep behavior (e.g., an injury-causing scenario in the patient's sleep), and the time (e.g., date and time of the day), and the number of occurrences of the abnormal sleep behavior is stored, such as on a smartphone, a computer, a tablet, etc., through wired, wireless, or USB communication. In some embodiments, each time the detected parameter is over a set criteria (e.g., the change in the parameter meets the set criteria), the system stores information such as the detected parameter, the parameter value, and/or the time of the day and the date in the storage device as one occurrence of the sleep disorder event. In an embodiment, the system may send a notification to another device to inform the caregiver, physician, etc. about the occurrence of the sleep disorder event. In an embodiment, the system may track and store total hours of sleep (e.g., total hours the detector is on), number of episodes of sleep disorder (e.g., total number of times the set criteria is reached), length of episode of sleep disorder (e.g., duration of time when set criteria is reached), magnitude and type of activity during episodes per night, week, month, year, etc. The physician may determine the effectiveness of a treatment based on the record of sleep disorder event, and adjust the medication or care plan based on the information. In some embodiments, the abnormal sleep behavior activity and/or date and time of the occurrence may be displayed as a list, a table, a graph, a bar chart, or similar formats. The adjusting medication may include changing in dosage and/or type of medication.

According to embodiments of the present disclosure, the system is utilized in characterizing abnormal sleep behavior and providing reliable and accurate information to aid physicians in diagnosis and creation of treatment plan; monitoring sleep behavior (e.g., during clinical trials) to objectively, consistently, systematically, and quantitatively measure efficacy of medical intervention; and informing changes to care plan.

Figure 6:
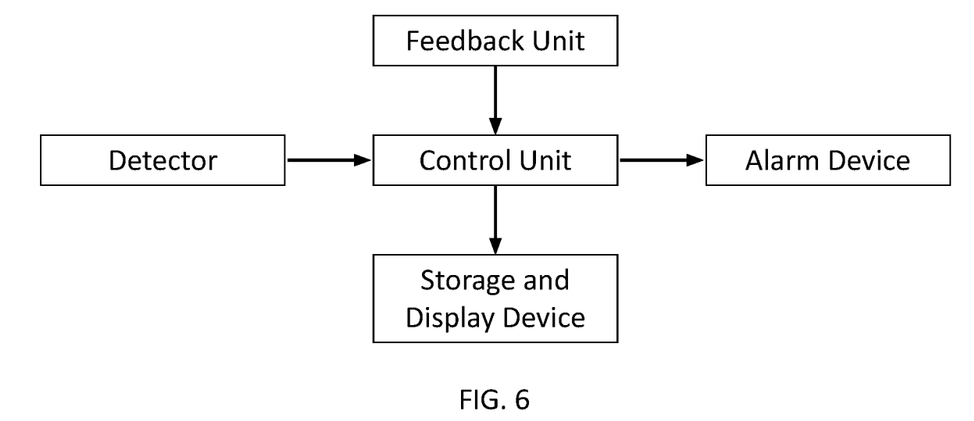
FIG. 6 is a schematic illustration of a system for monitoring a patient with sleep disorder according to an embodiment of the present disclosure.

According to embodiments of the present disclosure, a system includes a feedback loop to customize the set criteria. As shown in FIG. 6, the system includes a detector for detecting a change in a parameter, a control unit for deciding if the change meets a set criteria, an alarm device for waking the patient (e.g., sounding an alarm), a feedback unit for providing user feedback to the control unit, and a storage and display device for storing the parameter and type of activity and displaying the stored parameter and type of activity.

The detector, the parameter and the control unit may be substantially the same as the detector, the parameter and the control unit described above. The alarm device is substantially the same as the output device described above. In the current embodiment, a feedback unit is included to allow user (e.g., patient and/or caregiver) to report on accuracy of the system in detecting sleep disorder events. The user may indicate if an activation is false or correct, and/or if the system failed to activate during an abnormal sleep disorder event (e.g., jumping off the bed, sitting up in bed, moving violently while lying in bed, etc.). The control unit may take the input from the user and adjust the set criteria for activation through a feedback loop and replace the previous set criteria with the new set criteria (e.g., increasing or decreasing parameter threshold values, increasing or decreasing sensor sensitivity, removing or adding parameters, etc.).

Figure 7:
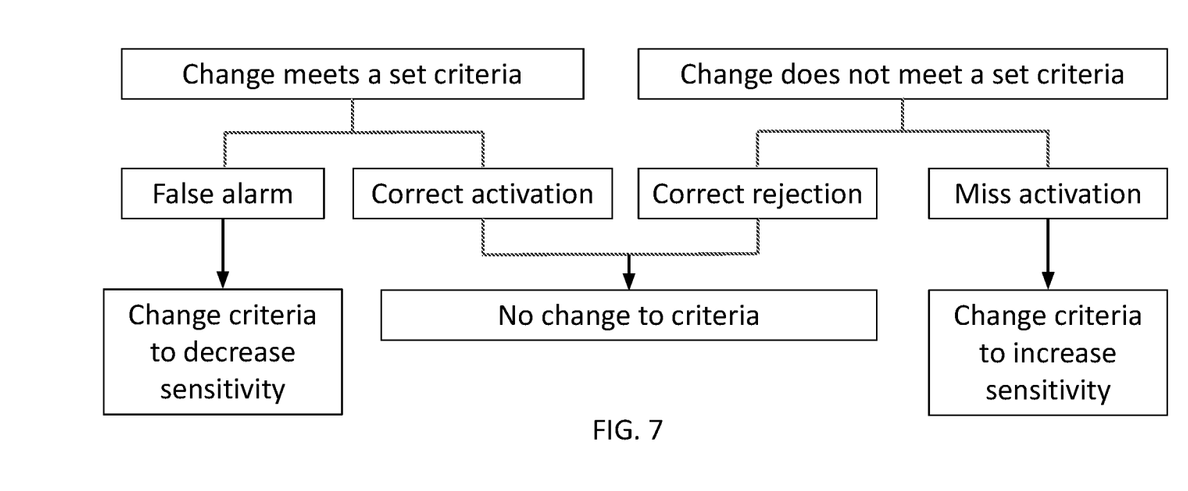
FIG. 7 is a flow chart illustrating a method of adjusting the set criteria according to an embodiment of the present disclosure.

FIG. 7 illustrates a flow chart for the feedback loop. After the system detects a change that meets the set criteria, the alarm is activated. The user decides if the activation is correct, and if so, informs the control unit that the system is activated accurately. If the activation is a false alarm, the user informs the control unit that it was a false alarm, and the system changes the set criteria to make the alarm activation happen at a higher degree of change of the detected parameter and reduce sensitivity of the system. Furthermore, when the alarm did not sound when a sleep disorder actually happened, the user informs the control unit that a sleep disorder event has been missed, and the control unit makes a change in the set criteria (e.g., reduces the set criteria to increase sensitivity of the system). If the user confirms that the non-activation is due to no sleep disorder event and the system correctly avoided activation of the alarm, then user may inform the control unit so no change in the set criteria is made. The feedback unit may have a designated button for each of the scenarios, e.g., false alarm, correct activation, correct non-activation (correct rejection) and missed alarm (failed to activate). In other embodiments, the system may include a user interface on the display (e.g., smartphone, laptop, computer, tablet, etc.) for making these inputs.

In some embodiments, the adjustment in the set criteria may be done manually by the user through a remote device, such as a smartphone or a computer. The smartphone may enable the adjustment in the set criteria in a custom-made application. In an embodiment, the change in the set criteria may be sent from the remote device to the control unit through wired, wireless, or USB communication. In other embodiments, the feedback unit may be the same device as the alarm device and/or monitoring and displaying device (e.g., smartphone, laptop, computer, tablet, etc.).

In some embodiments, the adjustment in the set criteria may be performed repeatedly based on the most recent feedback until the system accurately activates when needed without false alarm or missed activation. The adjustment in the set criteria may be done manually by the user (e.g., through adjusting the Arduino code, manually adjusting a dial on the device, etc.) or through machine learning, which can incorporate patient feedback (and/or other information) to automatically adjust threshold values to increase or decrease sensitivity.

In some embodiments, the method for patient monitoring and/or alerting includes selecting a parameter and determining the preset value (e.g., threshold value) utilizing machine learning. The method includes a learning process and an operating process. In an embodiment, a dataset including a number of parameters is collected and correlated with whether a sleep disorder event happened (e.g., dream enactment for RBD patient) over a period of time, e.g., 2 days, a week, etc. The parameters may include 3 or more, 4 or more, or all of sound, motion, heart rate, blood pressure, breathing frequency, magnitude and/or frequency of movement, muscle activity, brain activity, eye movements, heart rhythm, heart rate variability, blood oxygen levels, breathing pattern, and/or body position. The collected data set is split into a learning set and a test set.

During the learning process, the learning set is fed to the machine and at the end of the learning process (e.g., including the training process, validation process and/or evaluation process), the machine learning program identifies one or more parameters from the multiple parameters that are the most sensitive and accurate in predicting or detecting the occurrence of sleep disorder events, and their respective threshold values. In some embodiments, a single parameter is identified. In other embodiments, two or three parameters are identified as when utilizing together, provide the best accuracy in detecting sleep disorder events.

Figure 8:
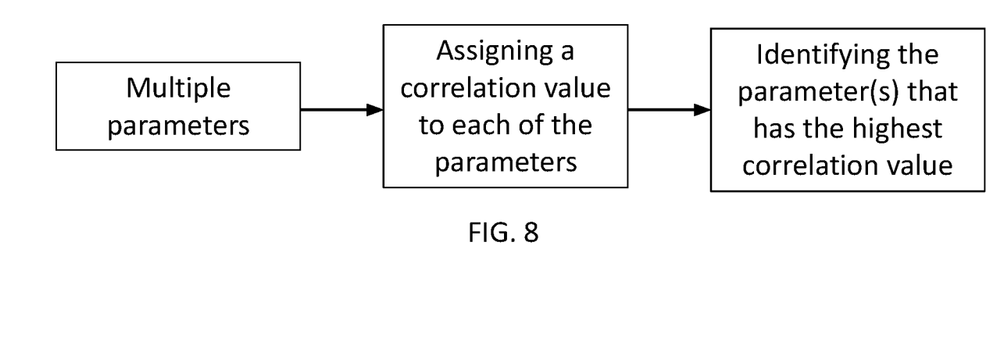
FIG. 8 is a schematic illustration of machine learning process.

FIG. 8 is a schematic illustration of machine learning process. Referring to FIG. 8, the method may include training the machine learning architecture to generate a model which designates a correlation value for each of the multiple parameters to represent their correlation to the corresponding occurrence of sleep disorder event, validating the correlation value and evaluating the correlation value. The training process and the validation process together are referred to as the learning process. The term "machine learning architecture" as used herein refers to the components of the machine learning process (e.g., neural networks), the matrix utilized, the fitting models, data collection and splitting, the algorithms utilized in the machine learning process, etc.

During the validation process, the test set of the dataset is utilized to provide an unbiased evaluation of the accuracy of the model. That is, the test data is processed to validate whether when the identified parameter met the threshold value indeed corresponds to a sleep disorder event at a degree matching the correlation value. When the result does not meet a set or preterminal evaluation criteria (e.g., 80% accuracy, 90% accuracy, etc.), the model parameters are adjusted through calculating the loss (i.e. error rate, or loss function) to improve the model accuracy. Depending on the machine learning algorithm, the evaluation criteria may be based on F1 score, mean squared error (MSE), root mean squared error (RMSE), etc. When the result meets the set or predetermined evaluation criteria, no further adjustment is made. A final model, i.e., the identified one or more parameters that are the most sensitive and has the strongest correlation (e.g., having the highest correlation value) to the sleep disorder event and threshold value(s) are obtained at the end of the validation process. In some embodiments, the parameter identification and the threshold value determination are conducted together in the machine learning process. In other embodiments, the parameter identification is conducted first, and the threshold value for the selected parameter is determined through a separate process, e.g., as shown in FIG. 7.

Then in the operating stage, only the parameter(s) (e.g., pitch of voice, rate of eye movement, or speed of arm movement) and the set criteria (e.g., the threshold value) that have been identified as the most sensitive and has the strongest correlation to the sleep disorder event are utilized for patient monitoring and/or alerting. In some embodiments, only a single parameter is utilized for the patient monitoring and/or alerting. In other embodiments, two or three parameters are utilized together for patient monitoring and/or alerting. In some embodiments, 5 or less, or 4 or less parameters are utilized together for patient monitoring and/or alerting.

Any suitable computing device, such as a computer, a laptop, etc., may be programmed to perform the machine learning.

According to some embodiments, the machine learning architecture may utilize a generative adversarial network (GAN), a deep convolutional neural network (DNN), or equivalent statistical learning algorithms. However, embodiments of the present disclosure is not limited thereto, and any suitable machine learning architecture may be utilized.

According to some embodiments, the device can monitor any number of the mentioned parameters in any combination. The machine learning function will identify which particular parameters are most indicative of abnormal sleep behavior to adjust and customize the combination of parameters for each patient. Once the set criteria is met for one or more of the parameters, the device will activate the alarm. The user can provide feedback through buttons or a user interface (e.g., smartphone application) on whether the device correctly activated, incorrectly activated, or failed to activate (e.g., missed activation) to abnormal sleep behavior. The device will automatically select which parameters are most indicative of abnormal sleep behavior. The device can then only monitor those parameters or use these parameters as the main parameters for alarm activation. The patient can also view on the display unit which parameters are most indicative of abnormal sleep behavior and choose to only use those parameter monitors. This mechanism will help to optimize the number and type of parameters needed to accurately detect abnormal sleep behavior for individual patients.

In some embodiments, the device will also have a machine learning function to adjust and customize the set criteria for each parameter. Once the set criteria is met for one or more the parameters, the device will activate the alarm. The user can provide feedback through buttons or a user interface (e.g., smartphone application) on whether the device correctly activated, incorrectly activated, or failed to activate to abnormal sleep behavior. The device will automatically adjust the set threshold to avoid failed activations and incorrect activations. Incorrect activations will result in decreasing the sensitivity of the set criteria, while failed activations will result in increasing the sensitivity of the set criteria. This mechanism will help to optimize the set threshold to accurately detect abnormal sleep behavior for individual patients.

In some embodiments, the device includes an option to disable the alarm when the device is utilized for diagnosis and/or monitoring of treatment effectiveness, and to enable the alarm when the device is utilized for alerting patients.

With the system according to embodiments of the present disclosure, the patient with sleep disorder can be woken up without the involvement of a caregiver, which may allow the caregiver to have a better sleep quality at night and also give the family members peace of mind when not physically close to the patient. Furthermore, the severity of the patient's condition, and the effectiveness of the medical intervention may be monitored in a home environment.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Expressions such as "at least one of," when preceding a list of elements, modify the entire list of elements and do not modify the individual elements of the list. Further, the use of "may" when describing embodiments of the inventive concept refers to "one or more embodiments of the inventive concept." Also, the term "exemplary" is intended to refer to an example or illustration.

The patient alert and/or monitoring system and/or any other relevant devices or components according to embodiments of the present invention described herein may be implemented utilizing any suitable hardware, firmware (e.g. an application-specific integrated circuit), software, or a combination of software, firmware, and hardware. For example, the various components of the patient alert system may be formed on one integrated circuit (IC) chip or on separate IC chips. Further, the various components of the patient alert system may be implemented on a flexible printed circuit film, a tape carrier package (TCP), a printed circuit board (PCB), or formed on one substrate. Further, the various components of the patient alert system may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the scope of the exemplary embodiments of the present invention.

What is claimed is:

1. A system of alerting and monitoring patient with sleep disorder, the system comprising:
a detector for detecting a change in a first parameter,
a storage device,
a control unit for deciding if the change meets a set criteria, and if the change meets the set criteria, saving the first parameter, time stamp, and duration in the storage device as one occurrence of sleep disorder event,
a feedback unit for adjusting the set criteria according to sleep behavior of the patient, and
an alarm device for sending an alarm comprising a customizable sound, and to be manually reset each time after activation,
wherein the first parameter comprises sound, motion, body position, and a duration of the motion,
wherein the change comprises increased volume of the patient's voice, and two times or more movements in 10 seconds, and
the movements consist of two or more of the following actions: waving arm, kicking leg, turning the body, changing body position by 15° or more in angle, or changing from a lying position to a sitting up or standing position.

2. The system of claim 1, wherein the detector comprises a motion sensor and an audio sensor.

3. The system of claim 1, wherein the control unit comprises a codable device.

4. The system of claim 1, wherein the feedback unit is to inform the control unit if the set criteria correctly correlates to sleep disorder event, and to trigger the control unit to increase or decrease the set criteria when there is false alarm or failed alarm.

5. The system of claim 1, wherein the control unit comprises a machine learning architecture.

6. A method of monitoring patient condition with sleep disorder, the method comprising: detecting a change in a first parameter, deciding if the change meets a set criteria, storing the first parameter, time stamp, and duration in a storage device if the change meets the set criteria as one occurrence of sleep disorder event, and sending an alarm comprising a customizable sound, wherein the first parameter comprises sound, motion, body position, and a duration of the motion, wherein the change comprises increased volume of the patient's voice, and two times or more movements in 10 seconds, and the movements consist of two or more of the following actions: waving arm, kicking leg, turning the body, changing body position by 15° or more in angle, or changing from a lying position to a sitting up or standing position.

7. The method of claim 6, further comprising:
adjusting the set criteria according to sleep behavior of the patient.

8. The method of claim 6, further comprising:
increasing the set criteria if there is false activation or decreasing the set criteria if there is failed activation.

9. The method of claim 6, further comprising: collecting a first dataset comprising a plurality of parameters, conducting a learning process in machine learning and selecting one or more parameters from the plurality of parameters to constitute the first parameter and a set criteria for each of the one or more parameters, and monitoring the patient utilizing only the first parameter and the set criteria in the detecting of the change in the first parameter, wherein the plurality of parameters comprises 3 or more selected from sound, motion, heart rate, blood pressure, breathing frequency, magnitude and/or frequency of movement, muscle activity, brain activity, eye movements, heart rhythm, heart rate variability, blood oxygen levels, breathing pattern, and body position.

10. The method of claim 6, further comprising:
sending an alert message to a physician or caregiver if the change meets the set criteria.

11. The method of claim 6, further comprising:
displaying information comprising a number of times the change meets the set criteria, a duration of time when set criteria is reached, and/or a magnitude and type of activity when set criteria is reached over a set number of days in order to characterize sleep disorder event.

12. The method of claim 6, further comprising disabling the alarm to monitor the patient condition.

13. A method of monitoring treatment effect for patient with sleep disorder, the method comprising: detecting a change in a first parameter, deciding if the change meets a set criteria, storing the first parameter, time stamp, and duration in a storage device if the change meets the set criteria as one occurrence of sleep disorder event and sending an alarm comprising a customizable sound, wherein the first parameter comprises sound, motion, body position, and a duration of the motion, wherein the change comprises increased volume of the patient's voice, and two times or more movements in 10 seconds, and the movements consist of two or more of the following actions: waving arm, kicking leg, turning the body, changing body position by 15° or more in angle, or changing from a lying position to a sitting up or standing position.

14. The method of claim 13, further comprising:
increasing the set criteria if there is false activation or decreasing the set criteria if there is failed activation.

15. The method of claim 13, further comprising: collecting a first dataset comprising a plurality of parameters, conducting a learning process in machine learning and selecting one or more parameters from the plurality of parameters to constitute the first parameter and a set criteria for each of the one or more parameter, and monitoring the patient utilizing only the first parameter and the set criteria in the detecting of the change in the first parameter, wherein the plurality of parameters comprises 3 or more selected from sound, motion, heart rate, blood pressure, breathing frequency, magnitude and/or frequency of movement, muscle activity, brain activity, eye movements, heart rhythm, heart rate variability, blood oxygen levels, breathing pattern, and body position.

16. The method of claim 13, further comprising:
comparing a number of events stored in the storage device with a preset number, and if the number of events is the same as or greater than the present number,
adjusting a medication and/or care plan.

17. The method of claim 16, wherein the adjusting the medication comprises increasing a dose of a medication, or changing a medication.

18. The method of claim 13, further comprising disabling the alarm to monitor treatment effectiveness.

\* \* \* \* \*